United States Patent [19]

Ponzi

[11] Patent Number: 4,480,461
[45] Date of Patent: Nov. 6, 1984

[54] VIBRATION INSTRUMENT

[75] Inventor: Joseph J. Ponzi, Alhambra, Calif.

[73] Assignee: International Telephone and Telegraph Corporation, New York, N.Y.

[21] Appl. No.: 478,432

[22] Filed: Mar. 24, 1983

[51] Int. Cl.$^3$ .............................................. G01N 9/00
[52] U.S. Cl. ..................................... 73/32 A; 29/525
[58] Field of Search ...................................... 73/32 A

[56] References Cited

U.S. PATENT DOCUMENTS

| | | | |
|---|---|---|---|
| 3,808,875 | 5/1974 | Miller | 73/32 A |
| 4,041,769 | 8/1977 | November | 73/32 A |
| 4,135,383 | 1/1979 | November | 73/32 A |

*Primary Examiner*—Gerald Goldberg
*Assistant Examiner*—John E. Chapman, Jr.

[57] ABSTRACT

Apparatus for producing an output signal or indication directly proportional to the density of one or more gases or liquids. A probe holds a vibrating vane immersed in a fluid. The probe is suspended from a pipeline flange by a boss that has upper and lower portions connected together by a thin annular cantilever-like disc in a plane transverse to the probe axis. The boss supports telescoped inner and outer cylinders along an axis normal to the probe axis. The cylinders have an interference fit. The outer cylinder has a uniform outside diameter but an unstressed inside diameter that increases in direct proportion to its length. The same is true of the outside diameter of the inner cylinder. The inner cylinder supports the vane. A seismic mass which vibrates the boss is unsupported except at one end.

12 Claims, 12 Drawing Figures

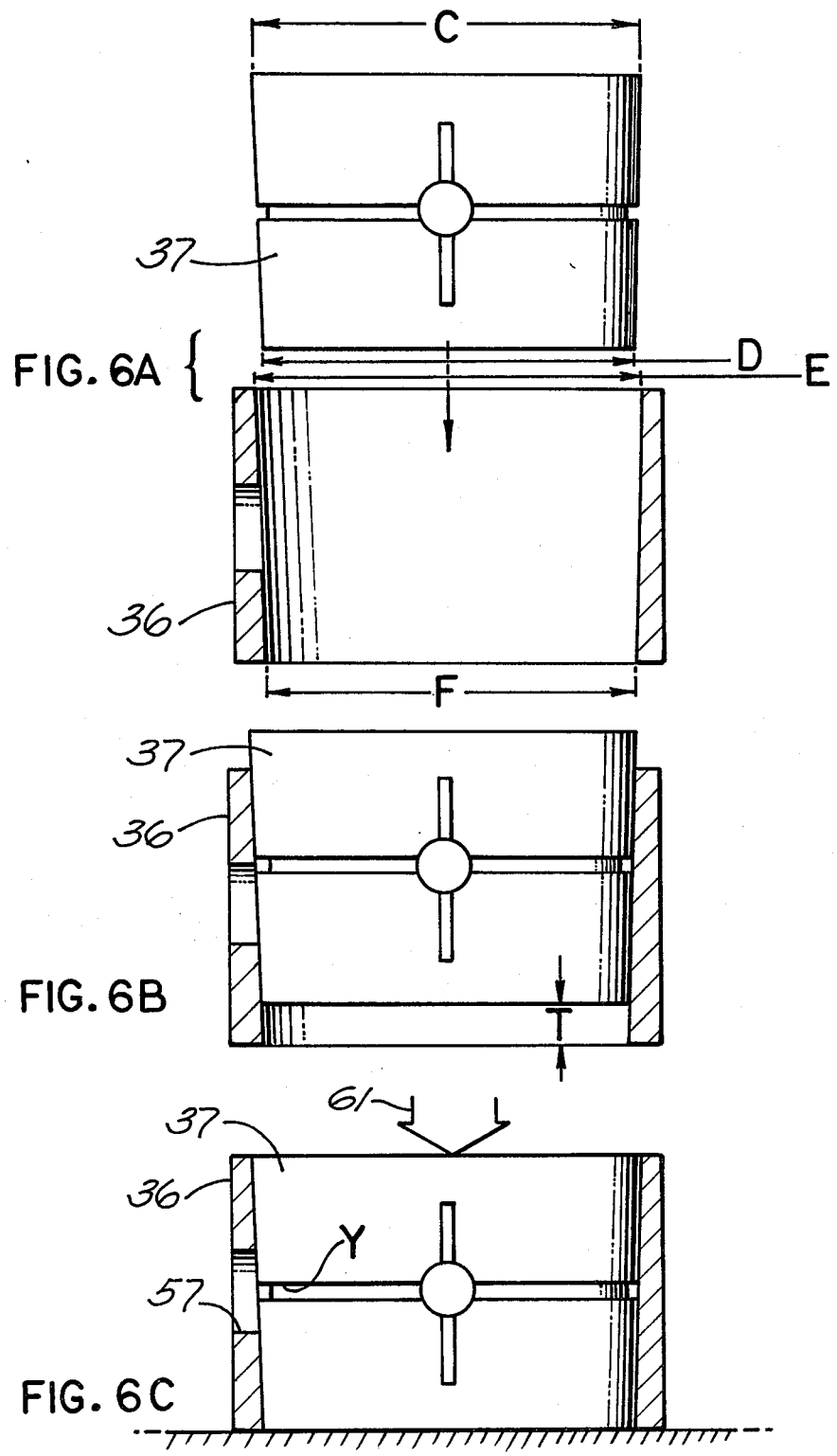

VIBRATION INSTRUMENT

BACKGROUND OF THE INVENTION

This invention relates to fluid density measurement, and more particularly to a vibration densitometer.

PRIOR ART STATEMENT

The instant invention is related to Miller U.S. Pat. No. 3,667,067 issued July 18, 1972 and a number of patents issued before or after the date thereof. For example, a seismic mass fixed with a jam nut is disclosed in Miller U.S. Pat. No. 3,741,000 issued June 26, 1973. See also Miller U.S. Pat. No. 3,805,361 issued Apr. 23, 1974; Miller U.S. Pat. No. 3,706,220 issued Dec. 19, 1972; November U.S. Pat. No. 4,041,769 (permanent magnet drive) issued Aug. 16, 1977. Further, see November U.S. Pat. No. 4,135,383 (FIG. 2, flange mount; FIG. 1, circuit) issued Jan. 23, 1979. See also the manner in which a magnetostrictive tube abuts the lower end of a probe boss in Ponzi U.S. Pat. No. 4,345,456 issued Aug. 24, 1982.

SUMMARY OF THE INVENTION

In accordance with the densitometer of the present invention, sensitivity and accuracy are improved, and vibration isolation are achieved.

The former is improved by providing a seismic mass support at the low end thereof and/or a cantilever-like support for the mechanical portions of a closed loop electromechanical oscillator.

Another outstanding feature of the present invention resides in a tapered interference fit between two cylinders, one of which supports a vibratable vane. The taper saves an exceedingly large amount of assembly effort. Further, performance is not impaired.

BRIEF DESCRIPTION OF THE DRAWINGS

In the accompanying drawings which illustrate exemplary embodiments of the present invention:

FIGS. 6A–6C are vertical sectional views, partly in elevation, showing how the probe is further assembled.

DESCRIPTION OF THE PREFERRED EMBODIMENT

Figure 1:
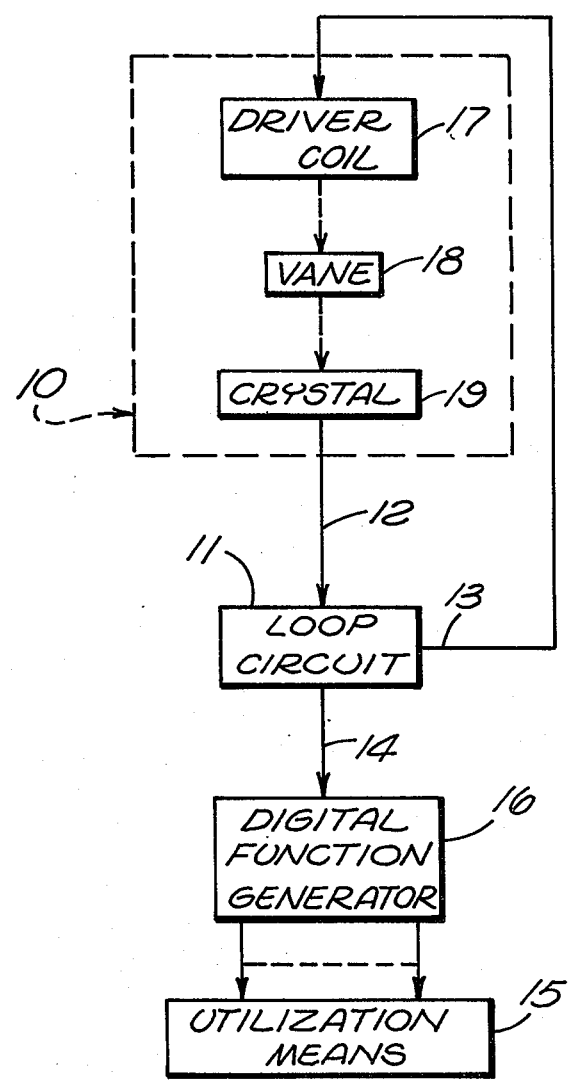
FIG. 1 is a block diagram of a densitometer constructed in accordance with the present invention.

A probe 10 is shown in FIG. 1 connected to and from a loop circuit 11 at 12 and 13, respectively. The output of loop circuit 11 on lead 14 is connected to utilization means 15 via a digital function generator 16.

Probe 10 contains a driver coil 17, a vane 18, and a crystal 19.

Everything shown in FIG. 1 may be conventional except the construction of probe 10. For example, see November U.S. Pat. No. 4,135,383 issued Jan. 23, 1979.

Utilization means 15 may be an indicator calibrated in units of density, if desired.

Crystal 19, per se, may be entirely conventional.

Digital function generator 16 may convert the output of loop circuit 11 to a linear function of density.

Probe 10 and loop circuit 11 together form a closed loop electromechanical oscillator with the probe 10 immersed in a fluid. The vane 18 then vibrates at a frequency which is a known function of the density of the fluid, and vice versa. A description of operation of the densitometer of FIG. 1 with a conventional probe may be found in November U.S. Pat. No. 4,135,383 or in one or more of the other patents cited herein.

There are several important advantages of the present invention related to three or more new structures in probe 10 to be described hereinafter.

Figure 2:
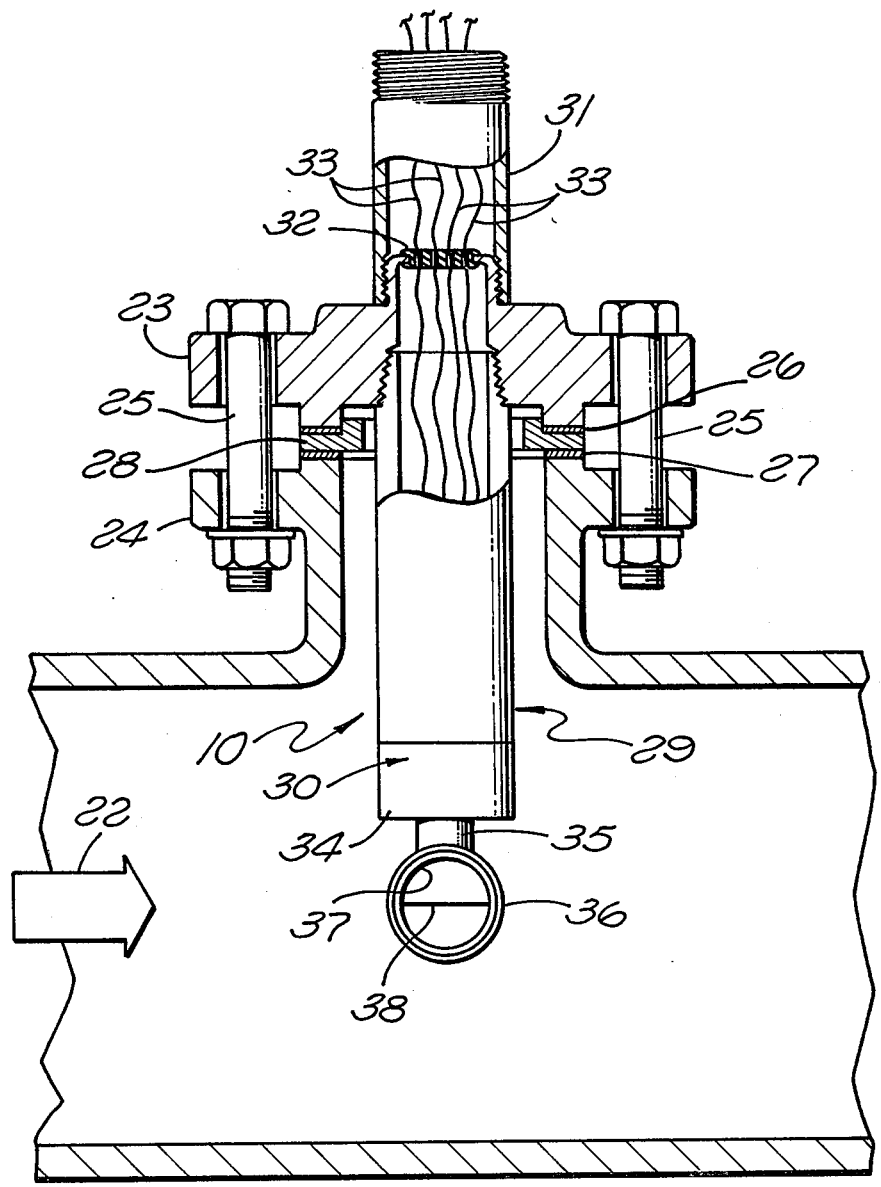
FIG. 2 is a longitudinal sectional view of a pipeline section and a densitometer probe constructed in accordance with the present invention.

Probe 10 is shown mounted in a pipeline 21 in FIG. 2. Flow may be as indicated by arrow 22.

Flanges 23 and 24 are bolted together at 25. Sealing gaskets are provided at 26, 27 and 28. A hollow cylindrical body 29 is threaded into and sealed to flange 23 and boss 30. See both of FIGS. 2 and 3.

A conduit 31 is provided that is threaded to flange 23. An hermetic seal 32 (pressure barrier) carries four wires 33.

Boss 30 has an upper portion 34 and a lower portion 35 comprising a probe head. Portion 35 is brazed to an outer cylinder 36 that, in turn, has an interference fit with an inner cylinder 37. A vane 38 is brazed to inner cylinder 37.

Figure 3:
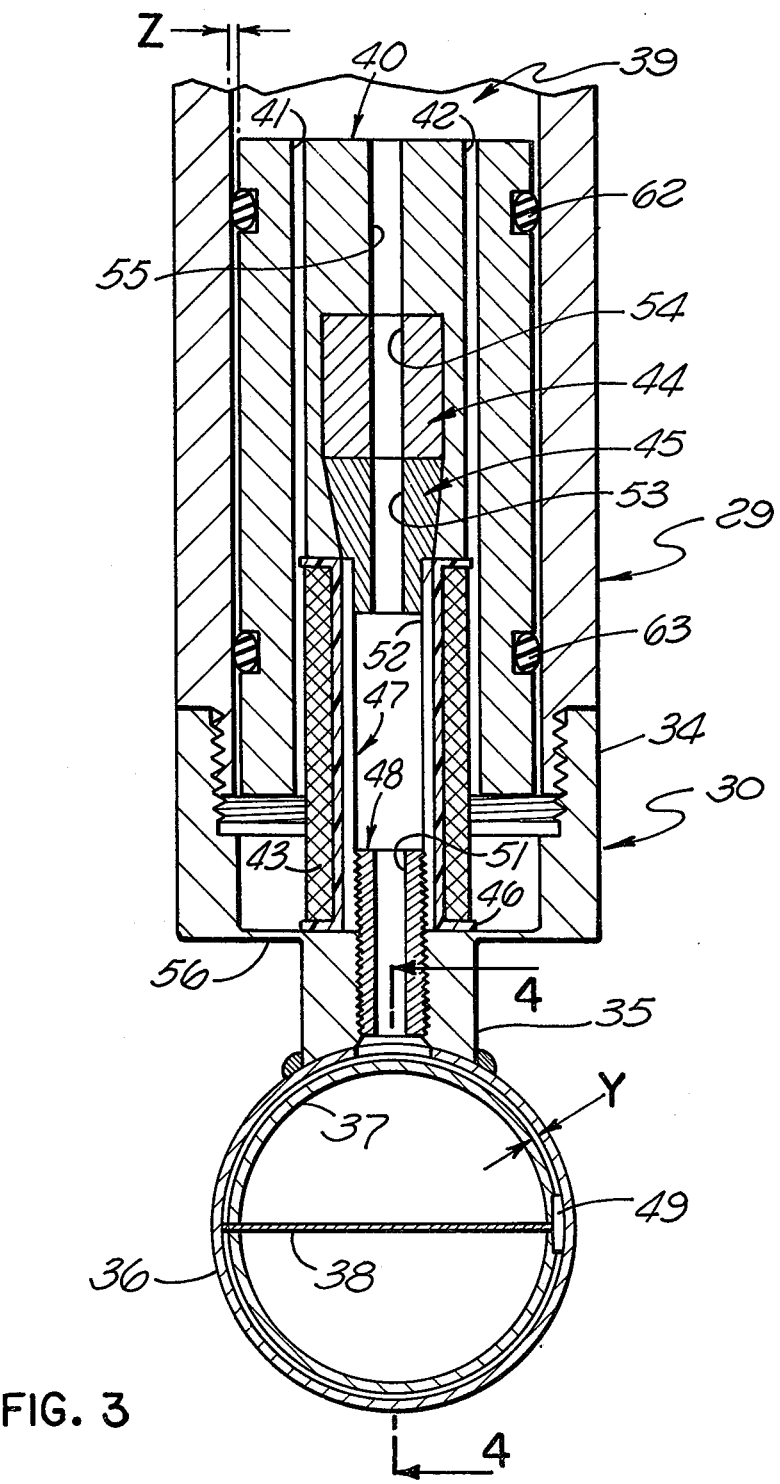
FIG. 3 is a vertical sectional view of the probe of FIG. 2.

Although some of the structures shown in FIG. 3 are known in the art, many have new and unique constructions and these new constructions have outstanding advantages.

A group of structures are fixed relative to each other in FIG. 3. These structures may be described as included in the seismic mass 39. Mass 39 is new because portion 40 is made of lead and because it is *everywhere* spaced at Z from the interior wall of body 29 except at O-rings 62 and 63. Mass 39 is concentric with the said interior. Portion 40 has holes 41 and 42 to carry respective wires from a solenoid at 43. The structure has resistance to side deformation (side impact and pipeline vibration). The structure is braced with flexible O-rings 62 and 63 (FIG. 3).

Seismic mass 39, before assembly into boss portion 35, has a magnet 44, pole piece 45, solenoid spool 46, solenoid 43, magnetostrictive cylinder 47 and hollow screw 48 fixed relative thereto. In accordance with the present invention, the lead of portion 40 is poured in molten form in a mold over magnet 44 etc.

After magnet 44 and the other structures are bonded to portion 40, screw 48 is threaded to and/or bonded to magnetostrictive cylinder 47. The seismic mass 39 can then be fixed relative to and/or bonded to boss 30 by threading screw 48 into portion 35 of boss 30. The lower end of spool 46 may then abut the upper end of boss portion 35. Cylinder 47 must firmly seat against top of portion 35, hence leave clearance for spool 46.

Lead wires (not shown) from a piezoelectric crystal 49 extend around in groove Y in cylinder 37 upwardly through passages 51, 52, 53, 54 and 55 respectively in screw 48, cylinder 47, pole piece 45, magnet 44 and seismic body portion 40.

One outstanding feature of the present invention resides in the "unsupported" seismic mass 39 (except at the bottom thereof).

Another outstanding feature of the present invention resides in the thin annular spring metal disc or diaphragm 56 (FIG. 3) that somewhat flexibly supports and isolates the main vibrating parts fixed relative to boss portion 35 below and directly above the same.

The present invention involves a new method and a new structure, both of which have further outstanding advantages. This new method and structure are illustrated in FIG. 4, FIGS. 5A–5E, and FIGS. 6A–6C.

Figure 4:
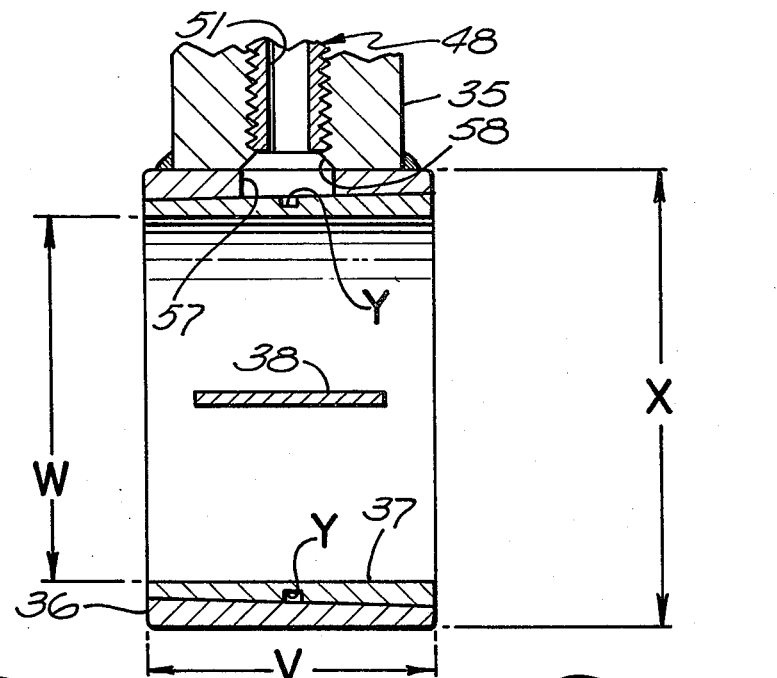
FIG. 4 is another vertical sectional view of the probe taken on the line 4—4 shown in FIG. 3.

In FIG. 4, wires (not shown) from crystal 49 (not shown) rest in groove Y, emanate therefrom, and extend upwardly through holes 57, 58 and 51.

The outside diameter of outer cylinder 36 is X and is constant along the entire length thereof. The same is true of the inside diameter W of inner cylinder 37. However, the inside diameter of outer cylinder 36 and the outside diameter of inner cylinder 37 are both slightly tapered. The tapers in FIG. 4 have been somewhat exaggerated for clarity.

The details of the assembly of vane 38 and inner cylinder 37 are shown in FIGS. 5A–5E. A vane blank 38' is moved through slots 59 and 60 that extend completely through the wall of cylinder blank 37' in FIG. 5A. Vane blank 38' is then brazed to cylinder blank 37' in FIG. 5B and the outside surface is machined to form vane 38 as shown in FIG. 5C. Groove Y is machined with a recess to receive crystal 49 as shown in FIG. 5D. The construction of cylinder 37 is then finished, and crystal 49 is bonded in place as shown in FIG. 5E.

Figure 5:
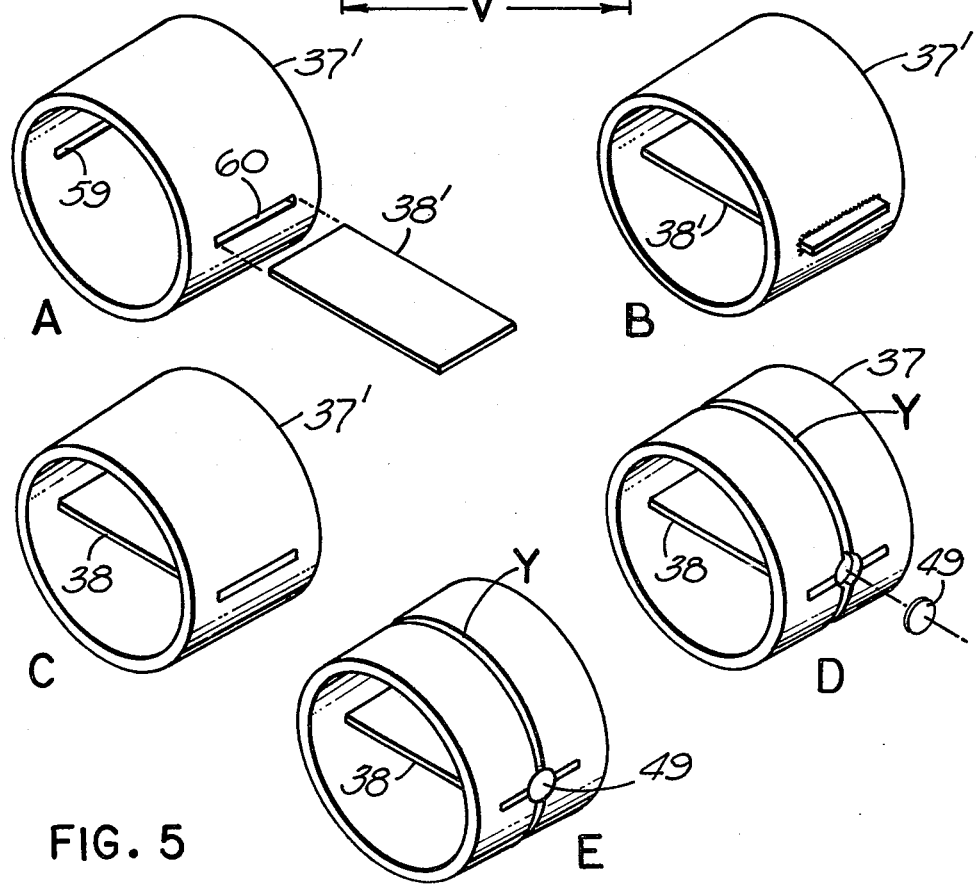
FIGS. 5A–5E are perspective views of portions of the probe in various stages of completion.

In FIGS. 5 and 6 one of the new and outstanding features of the present invention resides in the interference fit of the tapers of cylinders 36 and 37. See FIGS. 4 and 6. In FIG. 6A, C and D are the unstressed outside diameters of the respective larger and smaller ends of cylinder 37. Also in FIG. 6, E and F are the unstressed larger and smaller inside diameters of the respective larger and smaller ends of cylinder 36. Typically, from FIGS. 4 and 6A, in inches:

$V = 0.94$ $W = 1.187$ $X = 1.5$ $C = 1.336 + 0.008 = 1.344$ $E = 1.335 + 0.008 = 1.343$ $D = 1.336$ $F = 1.335.$

The unstressed tapered surfaces of cylinders 36 and 37 have corresponding diameters along their lengths x of $d_i$ and $d_o$. And $d_i/d_o \simeq 0.99925$ where $d_i$ and $d_o$ are the minimum diameters thereof. Typically, $d_o - d_i \simeq 0.001$ inch. $d_o$ and $d_i$ vary linearly with x.

Another feature of the present invention resides in an easier and a less expensive way to put cylinders 36 and 37 together. In FIG. 6, cylinder 37 is loosely guided into cylinder 36 to the position shown at T in FIG. 6B. The dimension T may be 0.118 inch with the above dimensions. With less interference fit, T can be less.

Then, with force, as indicated by arrow 61 in FIG. 6C, cylinder 37 is pressed into or press fit into cylinder 37 as shown, wherein each adjacent pair of the end surfaces of the cylinders lie in the same plane. Crystal leads can be threaded around cylinder 37 in groove Y outwardly of hole 57.

Disc 56 and its thin character helps to isolate lower boss portion 35, and everything connected therewith and to keep the same free from external vibrational interference and from external and internal noise. The same is true of the seismic mass 39 which does not touch upper boss portion 34 or anything thereabove except as shown, and touches only the top of lower boss portion 35 and is fixed relative thereto by screw 48.

It is a unique method of the present invention that permanent magnet 44, pole piece 45, spool 46, coil 43, and hollow screw 48 are fixed together, i.e. fixed relative to each other, and embedded in lead body 40 by pouring molten lead therearound, for example, in a mold.

Another outstanding feature of the present invention resides in the taper of the inside diameter of the outer cylinder 36 and the taper of the outside diameter of the inner cylinder 37. Among other advantages, it is possible to produce an interference fit between the said cylinders 36 and 37 simply by producing a press fit with a conventional arbor press. This eliminates cost and reduces manufacturing time required in the prior art. For example, see the details described in Miller U.S. Pat. No. 3,667,067 issued July 18, 1972.

Screw 48 may be threaded to and/or brazed to magnetostrictive tube 47. The seismic mass 39 then may be fixed relative to lower boss portion 35 by threading screw 48 into the said lower boss portion 35 and/or brazing the same thereto.

Note that the lower end of lower boss portion 35 is brazed to the outer cylinder 36.

A conventional shield and/or well may or may not be provided, if desired.

All densitometers of the present invention may be manufactured in many different sizes. Some dimensions may be as follows. Vane 38 may have a length of 1.344 inch centered along the length of the inner cylinder 37, a width of 0.625 inch, and a thickness of 0.028 inch.

Typically, the inside diameter of probe body 29 is 0.125 inch or 0.25 larger than seismic mass 39.

One outstanding advantage of the present invention resides in the improved sensitivity and efficiency of the closed loop electromechanical oscillator. With disc 56, a 10 volt input to coil 43 will produce an equivalent 8 volt output from crystal 49. With the disc 56 at the location shown in November U.S. Pat. No. 4,135,383, a coil voltage of 60 volts would produce an equivalent crystal voltage of 2 volts.

The use of a permanent magnet, pole piece and magnetostrictive tube is explained in U.S. Pat. No. 4,041,769 issued Aug. 16, 1977.

Each pair of the adjacent end surfaces of cylinders 36 and 37 lie in respective planes.

If the inside diameter of the outer cylinder 36 is $d_i$ at point x along the length thereof, and $d_o$ is the outside diameter of the inner cylinder 37 at x, $d_o$-$d_i$ may be a constant amount independent of x.

The diameter of the internal surface of the outer cylinder increases at a constant rate along the length thereof, and the diameter of the external surface of the inner cylinder increases at the same constant rate along the length thereof.

What is claimed is:

1. A vibration densitometer comprising: a probe including a head; a rectangular vane having parallel sides fixed relative to said head; and a closed loop electromechanical oscillator including a sensor to detect the frequency of vibration of said vane, a driver to vibrate said head and said vane, and means to energize said driver, said driver causing said head to vibrate along a first axis, a first hollow cylinder, a second hollow cylinder telescoped inside said first hollow cylinder, said first hollow cylinder being fixed to the end of said head, said first and second cylinders having a common symmetrical second axis, said first hollow cylinder being fixed to said head with an orientation such that said second axis lies normal to said first axis, said vane being fixed approximately in a diametral plane across the interior of said second hollow cylinder, said vane sides being fixed at respective positions around the interior wall of said second hollow cylinder, said first and second hollow cylinders having an interference fit, the interior surface of said first hollow cylinder having a taper such that the diameter at one end thereof is greater than that at the other end thereof, said second hollow cylinder having an external surface of a shape nesting inside said first hollow cylinder, the exterior of said second hollow cylinder having a taper such that the diameter thereof at said first cylinder one end is greater than the diameter thereof at said first cylinder other end.

2. The invention as defined in claim 1, wherein the diameter of the internal surface of said first cylinder increases at a constant rate along the length thereof, and wherein the diameter of the external surface of said second cylinder increases at the same said constant rate along the length thereof.

3. The invention as defined in claim 2, wherein the minimum unstressed diameter $d_i$ of said first cylinder internal surface is about 0.99925 the minimum unstressed diameter $d_o$ of said second cylinder external surface.

4. The invention as defined in claim 3, wherein $d_o - d_i \simeq 1$ mil.

5. The invention as defined in claim 4, wherein each adjacent pair of the end surfaces of said cylinders lie in the same plane.

6. The invention as defined in claim 5, wherein said second cylinder has diametrically opposite slots through the wall thereof and parallel to said second axis midway along the length of said second cylinder, said vane having its ends fitted into respective ones of said second cylinder slots and fixed relative to said second cylinder.

7. The invention as defined in claim 2, wherein the inside diameter $d_i$ of said first cylinder at any point x along the length thereof is smaller than the outside diameter $d_o$ of said second cylinder by a constant amount when both of said cylinders are unstressed.

8. The invention as defined in claim 7, wherein each adjacent pair of the end surfaces of said cylinders lie in the same plane.

9. A vibration densitometer comprising: inner and outer essentially concentric cylinders with one axis and having an interference fit; a boss having a lower cylindrical portion having a lower end fixed to said outer cylinder, said lower portion having an axis normal to said one axis, said boss having an upper cylindrical portion concentric with said lower portion thereabove; an annular disc fixed between said lower portion upper end and the lower end of said upper portion, said disc being fixed between said portions approximately in a plane normal to said lower portion axis, said disc being thin in the direction of the lower portion axis as compared to the wall thicknesses of said lower and upper portions in a radial direction from the lower portion axis; a vane fixed relative to said inner cylinder approximately through said one axis and normal to said lower portion axis; a piezoelectric crystal fixed relative to said vane; and closed loop electromechanical oscillator means responsive to the output of said crystal for vibrating said lower portion, said cylinders and said vane, said disc being an annular spring to support resiliently said lower portion, said cylinders and said vane from said upper portion.

10. The invention as defined in claim 9, wherein said oscillator means includes a seismic mass and a magnetostrictive tube having its upper end fixed to said mass and its lower end in pressure contact with the upper end of said lower portion.

11. A vibration densitometer comprising: inner and outer essentially concentric cylinders with one axis and having an interference fit; a boss having a lower cylindrical portion having a lower end fixed to said outer cylinder, said lower portion having an axis normal to said one axis, said boss having an upper cylindrical portion concentric with said lower portion thereabove; an annular disc fixed between said lower portion upper end and the lower end of said upper portion; means to hold said lower and upper portions in positions fixed relative to each other; a vane fixed relative to said inner cylinder approximately through said one axis and normal to said lower portion axis; a piezoelectric crystal fixed relative to said vane; and closed loop electromechanical oscillator means responsive to the output of said crystal for vibrating said lower portion, said cylinders and said vane, said oscillator means including a seismic mass and a magnetostrictive tube having its upper end fixed to said mass; and means to hold said tube in pressure contact with the upper end of said lower portion.

12. The invention as defined in claim 11, wherein said seismic mass is unsupported except upon an annular surface at the top of said lower portion.

* * * * *